(12) United States Patent
Qureshi et al.

(10) Patent No.: US 8,361,085 B2
(45) Date of Patent: *Jan. 29, 2013

(54) SYSTEMS AND METHODS FOR HARVESTING AND IMPLANTING HAIR USING IMAGE-GENERATED TOPOLOGICAL SKIN MODELS

(75) Inventors: Shehrzad A. Qureshi, Palo Alto, CA (US); Miguel G. Canales, Los Altos, CA (US)

(73) Assignee: Restoration Robotics, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/242,511

(22) Filed: Sep. 23, 2011

(65) Prior Publication Data

US 2012/0039516 A1  Feb. 16, 2012

Related U.S. Application Data

(62) Division of application No. 12/402,355, filed on Mar. 11, 2009, now Pat. No. 8,048,090.

(51) Int. Cl.
*A61B 17/3205* (2006.01)
(52) U.S. Cl. ........................................ 606/133
(58) Field of Classification Search .......... 606/133
See application file for complete search history.

(56) References Cited

U.S. PATENT DOCUMENTS

| | | | |
|---|---|---|---|
| 5,251,127 A | 10/1993 | Raab | |
| 5,865,744 A | 2/1999 | Lemelson | |
| 6,013,087 A | 1/2000 | Adams et al. | |
| 6,027,512 A | 2/2000 | Bridges | |
| 6,572,625 B1 | 6/2003 | Rassman | |
| 6,585,746 B2 | 7/2003 | Gildenberg | |
| 7,172,604 B2 | 2/2007 | Cole | |
| 2005/0245952 A1 | 11/2005 | Feller | |
| 2005/0267506 A1 | 12/2005 | Harris | |
| 2006/0161179 A1 | 7/2006 | Kachenmeister | |
| 2006/0178678 A1 | 8/2006 | Cole | |
| 2007/0078466 A1 | 4/2007 | Bodduluri et al. | |
| 2007/0106306 A1 | 5/2007 | Bodduluri et al. | |
| 2007/0149985 A1 | 6/2007 | Cole | |
| 2007/0156164 A1 | 7/2007 | Cole et al. | |
| 2007/0213741 A1 | 9/2007 | Cole | |
| 2008/0234698 A1 | 9/2008 | Oostman et al. | |
| 2009/0012536 A1 | 1/2009 | Rassman et al. | |

FOREIGN PATENT DOCUMENTS

| WO | 2007041267 | 4/2007 |
|---|---|---|
| WO | 2009148922 | 12/2009 |

OTHER PUBLICATIONS

Kuniyoshi Yagyu, MD; Koki Hayashi, MD; and Steven C. Chang, MD. Orientation of Multi-Hair Follicles in Nonbald Men: Perpendicular Versus Parallel. Dermatol Surg 2006; 32: pp. 651-660. Published by Blackwell Publishing.

(Continued)

*Primary Examiner* — Ryan Severson
(74) *Attorney, Agent, or Firm* — Lena I. Vinitskaya

(57) ABSTRACT

Systems and methods are provided for orienting a hair harvesting tool relative to a follicular unit to be harvested. Further, systems and methods of implanting follicular units are provided, which are based on the orientation of the existing follicular units or based on predetermined insertion angle. The provided systems and methods use image processing and image-generated topological skin models. In some embodiments surface fit is performed using, for example, a planar fit, quadric fit, cubic fit, mesh fit and parametric fit.

22 Claims, 7 Drawing Sheets

OTHER PUBLICATIONS

Mohammed Alhaddab, MD; Thomas Kohn, MD; and Mark Sidloi, BSc. Effect of Graft Size, Angle, and Intergraft Distance on Dense Packing in Hair Transplant. Dermatol Surg 2005; 31: pp. 650-654. Published by BC Decker Inc.

Robert M. Bernstein, MD; William R. Rassman, MD. "New Instrumentation for Three-Step Follicular Unit Extraction". Hair Transplant Forum International, vol. 16, No. 1, Jan./Feb. 2006.

PCT International Search Report in relation to commonly assigned PCT application, PCT/US2010/026102, Applicant: Restoration Robotics, Inc., Forms PCT/ISA/210, 220 and 237, dated Jun. 22, 2010 (11 pages).

James A. Harris, MD, FACS. "New Methodology and Instrumentation for Follicular Unit Extraction: Lower Follicle Transection Rates and Expanded Patient Candidacy." Dermatol Surg 32:1:Jan. 2006.

Robert M. Bernstein, MD; William R. Rassman, MC; Nazia Rashid; Richard C. Shiell, MBBS. The Art of Repair in Surgical Hair Restoration Part 1: Basic Repair Strategies. Dermatol Surg 28:9:Sep. 2002 pp. 783-794 (12 pages).

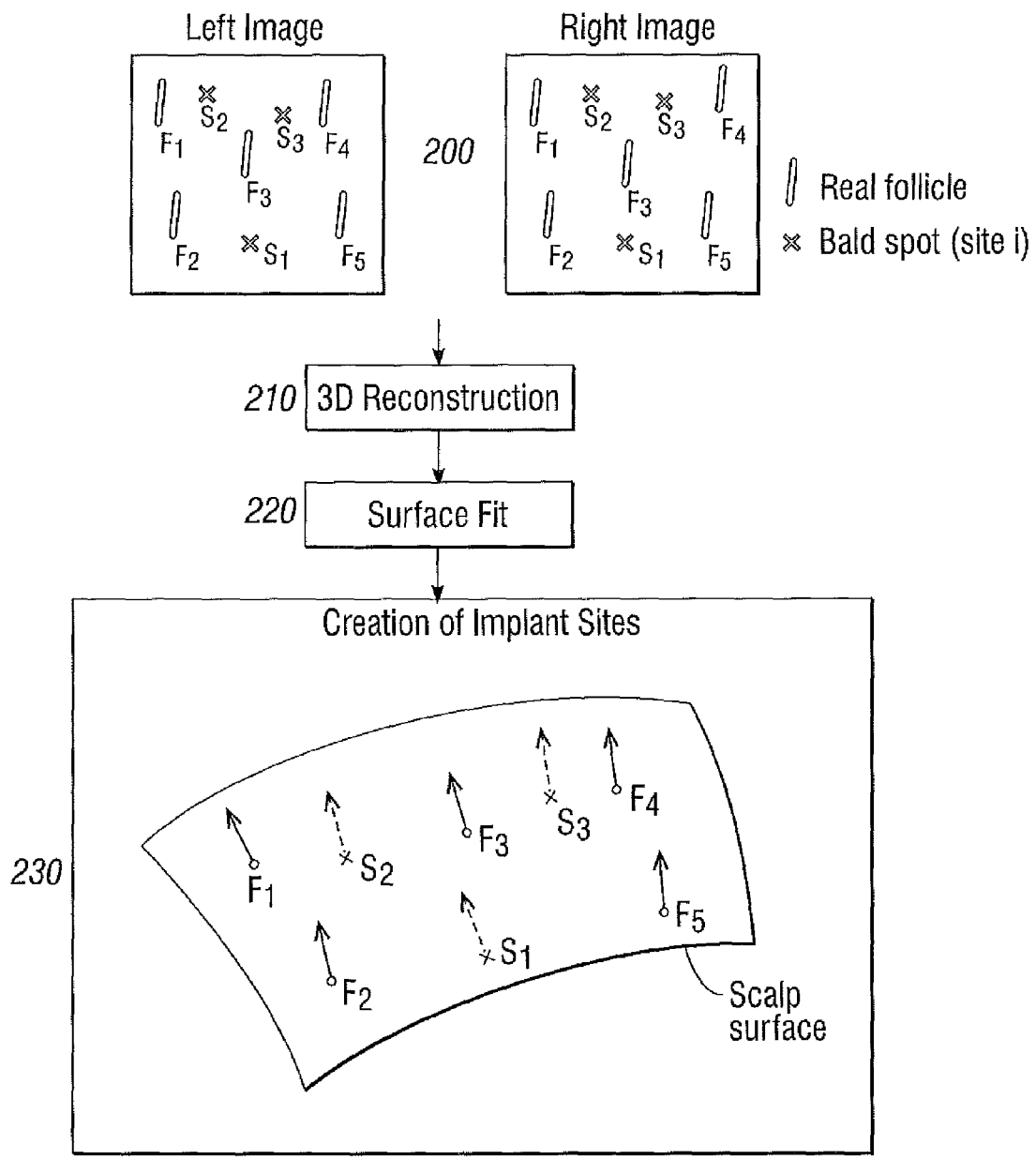

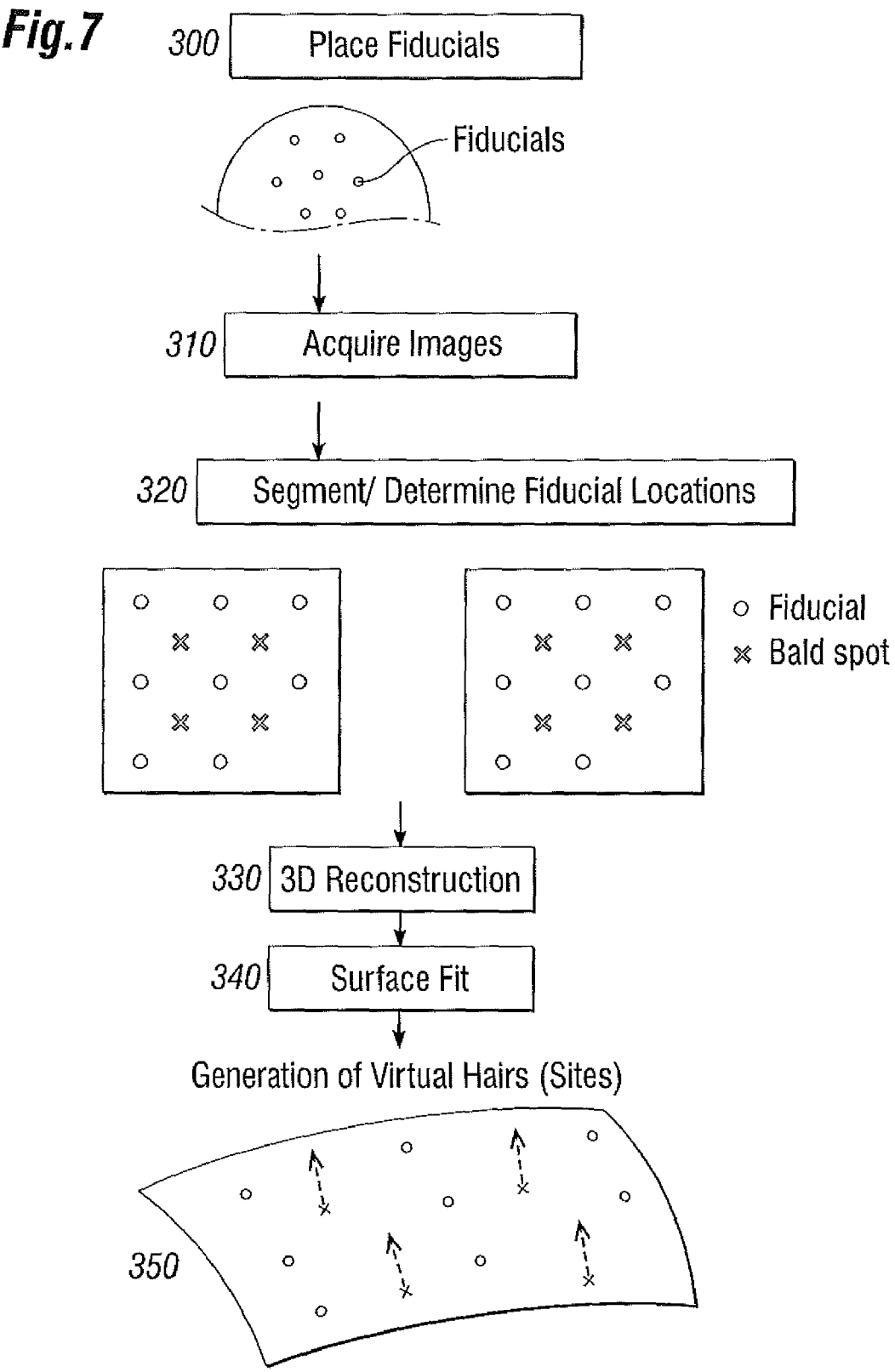

SYSTEMS AND METHODS FOR HARVESTING AND IMPLANTING HAIR USING IMAGE-GENERATED TOPOLOGICAL SKIN MODELS

RELATED APPLICATION DATA

The present application is a division of U.S. patent application Ser. No. 12/402,355, entitled "System and Method for Harvesting and Implanting Hair using Image-Generated Topological Skin Models," filed Mar. 11, 2009, now U.S. Pat. No. 8,048,090."

FIELD OF THE INVENTION

This invention relates generally to systems and methods for hair harvesting, implantation and transplantation and, in particular, to devices and techniques that allow reducing potential damage to and maintaining the integrity of the harvested hair follicles.

BACKGROUND OF THE INVENTION

Hair transplantation procedures are well-known, and typically involve harvesting donor hair grafts from the "donor areas," for example, side and back fringe areas of the patient's scalp, or other body surfaces, and implanting them in a bald area ("recipient area"). Various techniques were developed over the years for harvesting donor hair grafts. One such technique involves excising a strip of skin from the back area of the scalp and then dissecting the strip under a microscope to isolate individual hair follicular units for later implantation into the recipient area. This technique suffers numerous disadvantages, including being very time consuming, tedious, expensive, and requiring suturing and resulting scarring. Recently some physicians employ a technique called Follicular Unit Extraction ("FUE") that allows harvest of individual follicular units without a need to cut a strip of tissue from the patient's scalp.

An FUE method for harvesting follicular units allows for individual follicular units to be harvested directly from the donor area by utilizing a hollow punch having a cutting edge and an interior lumen with a diameter of, for example, 1 mm. The punch is used to make a small circular incision in the skin around the follicular unit. Thereafter, the follicular unit is removed, e.g., using forceps, for subsequent implantation into a recipient site with a specially devised insertion needle. FUE procedure avoids scarring associated with cutting a strip of scalp, reduces patient's discomfort, and reduces recovery time, however, it is a laborious procedure, take a long time to perform and it requires a high degree of technical skill.

U.S. Pat. No. 6,572,625 (the "Rassman patent") describes a particular mechanism for an alignment of hair follicles with the hollow harvesting punch during the FUE procedure. The harvesting procedure described in the Rassman patent teaches the users to align an axis of the harvesting instrument along the axis of the follicular unit to be extracted.

SUMMARY OF THE INVENTION

According to one aspect of the invention, a method for orienting a tool for harvesting follicular units with a follicular unit to be harvested is provided. In some embodiments, the method comprises determining an emergence angle of a FU of interest; choosing a minimal approach angle of a tool for harvesting follicular units; comparing the emergence angle of the FU of interest with the minimum approach angle of the tool; and orienting the tool relative to the FU of interest based on a result of the comparison of the emergence angle of the FU of interest with the minimum approach angle of the tool. In some embodiments, orienting the tool comprises automatically moving a robotic aim to which the tool is operatively connected. In other embodiments, orienting the tool comprises manually orienting a hand-held tool, for example, by actuating an adjustment mechanism.

According to another aspect of the invention, a method for harvesting follicular units from a body surface is provided. Such method comprises positioning a harvesting tool having a lumen over a FU to be harvested, the FU having an elongated axis; orienting the harvesting tool relative to the elongated axis of the FU based on a result of a comparison of an emergence angle of the FU with a selected minimum approach angle of the harvesting tool; inserting the harvesting tool into the body surface about the FU to be harvested; and removing the FU.

According to still another aspect of the invention, a method for orienting a tool for transplanting follicular units relative to a body surface is provided. In some embodiments the method comprises determining an emergence angle of a FU of interest; selecting or using a pre-selected minimum approach angle of a tool; comparing the emergence angle of the FU of interest with the minimum approach angle of the tool; and orienting the tool relative to the FU of interest based on a result of the comparison of the emergence angle of the FU of interest with the minimum approach angle of the tool. In some embodiments, the tool is a hair implantation tool and the method is directed to orienting the hair implantation tool relative to the implantation site.

According to a further aspect of the invention, another method for orienting a tool for implanting follicular units is provided. This method is especially useful when there is none or a very limited number of the pre-existing follicular units present at the implantation site. In some embodiments, the method comprises using fiducial markers to generate one or more virtual FUs having an emergence angle; selecting or using a pre-selected minimum approach angle of a implanting tool for implanting follicular units; identifying the emergence angle of the one or more virtual FUs to be not less than the minimum approach angle of the implanting tool; and orienting the implanting tool with the identified emergence angle of the one or more virtual FUs.

A yet further aspect of the invention provides a system for hair transplantation, comprising an interface adapted to receive an image data containing a follicular unit (FU); and an image processor comprising one or more modules for executing operations on the image data, the one or more modules including instructions for determining an emergence angle of the FU; selecting a minimal approach angle of a tool for harvesting follicular units; comparing the emergence angle of the FU with the minimum approach angle of the tool; and orienting the tool relative to the FU based on a result of the comparison of the emergence angle of the FU of interest with the minimum approach angle of the tool. The system may further include an image acquisition device. In some embodiments, the system is a robotic system, in other embodiments the system is configured for use with hand-held hair transplantation devices.

Another system of the present invention comprises an image acquisition device and a processor, the processor configured for determining an emergence angle of a FU of interest; choosing a minimal approach angle of a tool for harvesting follicular units; comparing the emergence angle of the FU of interest with the minimum approach angle of the tool; and orienting the tool relative to the FU of interest based on a result of the comparison of the emergence angle of the FU of interest with the minimum approach angle of the tool.

An article of manufacture comprising a machine-accessible medium including data that, when accessed by a machine, cause the machine to perform operations, comprising determining an emergence angle of a FU of interest, the FU of interest; choosing a minimal approach angle of a tool for harvesting follicular units; comparing the emergence angle of the FU of interest with the minimum approach angle of the tool; and orienting the tool relative to the FU of interest based on a result of the comparison of the emergence angle of the FU of interest with the minimum approach angle of the tool.

Systems and methods of the present invention may be implemented for use with manual, partially automated and fully automated, including robotic, systems and procedures for removal of biological units, including hair harvesting and/or transplantation. Other and further objects and advantages of the invention will become apparent from the following detailed description when read in view of the accompanying figures.

BRIEF DESCRIPTION OF THE DRAWINGS

Features and advantages of the present invention will become appreciated as the same become better understood with reference to the specification, claims, and appended drawings wherein:

FIG. 6 is a schematic depiction of one example of use of the surface fit modeling in hair implantation according to the invention;

FIG. 7 is a schematic depiction of another example of use of the surface fit modeling in hair implantation according to the invention.

DETAILED DESCRIPTION OF THE PREFERRED EMBODIMENTS

Figure 1:
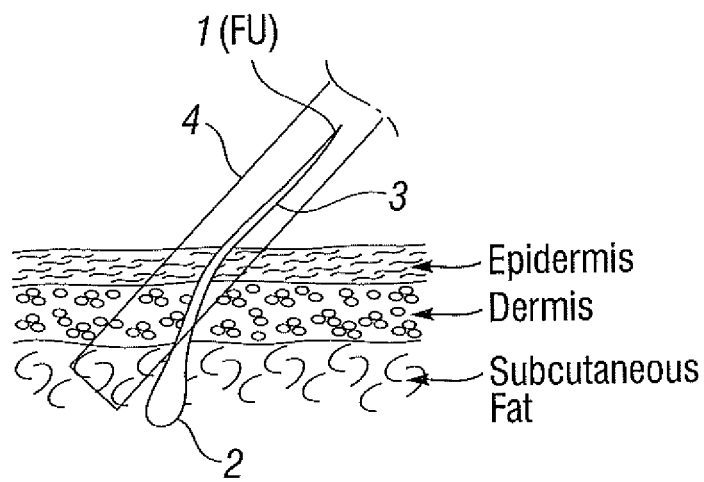
FIG. 1 illustrates follicular unit extraction method according to the prior art and hair follicle transaction associated with such method.

In the following Detailed Description, reference is made to the accompanying drawings that show by way of illustration some exemplary embodiments in which the invention may be practiced. In this regard, directional terminology, such as "top," "bottom," "front," "back," "distal," "proximal," etc., is used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following description, therefore, is not to be taken in a limiting sense, and the scope of the present invention is defined by the appended claims.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some of the automated systems described herein may also be robotically-assisted or computer/software/machine-instruction controlled. The devices and methods of the present invention are useful in manual procedures and systems, as well as in automated procedures and system. The tools of the present invention could be used with the robotically-assisted systems and procedures. The adverb "automatically" when referring to use of a particular component of a system or a particular step in a process means that such step is accomplished autonomously, i.e., without real-time manual assistance.

The term "tool," or "harvesting tool," or "implanting tool" as used herein refers to any number of tools or end effectors that are capable of removing or harvesting follicular units ("FUs") from a body surface, or implanting FU into the body surface. In this sense, a body surface can be attached to the body or may be a flap of skin or body tissue removed from the body. Such tools may have many different forms and configurations. In many embodiments, the tool comprises a hollow tubular shaft and thus may be labeled, for example, a cannula, a needle, or a punch. The terms "operatively connected," "coupled," or "mounted," or "attached" as used herein, means directly or indirectly coupled, attached, or mounted through one or more intervening components.

As mentioned above, though the invention is particularly useful in hair harvesting and implantation to provide devices and methods for harvesting and implanting follicular units (FUs), it is not limited to hair transplantation. Other procedures that require a model of the patient's skin surface, where said skin surface is assumed to have some hair, may benefit from the system and method of the inventions described herein. One example of applicability of the invention is in diagnostic skin imaging for cosmetic or other medical purposes. In some applications, the invention may be used with a vision system designed to track hair growth over a long period of time (e.g. each individual hair receives a fingerprint, with one part of this fingerprint being the hair's natural emergence angle).

FIG. 1 illustrates certain problems associated with the existing devices for follicular unit harvesting. During follicular extraction technique, the operator aligns a harvesting punch substantially parallel with the visible portion of the hairs protruding above the skin, for example, as described in U.S. Pat. No. 6,572,625. The punch is then pushed into the skin, often with significant force. As seen in FIG. 1, each follicle 1 of the follicular unit ("FU") has a hair bulb 2 (a subsurface bottom-most portion) and a hair shaft 3, the hair shaft extends through the epidermis, dermis and subcutaneous fat layers of the skin. The hair bulb 2 represents one of the critical structures of the follicle that contain follicular stem cells and melanocytes, other critical structures (not shown) include, for example, sebaceous glands, outer root sheath.

When harvesting follicular units for subsequent implantation in another area, it is important not to damage these critical structures.

One of the limitations, however, of the FUE-based devices and methods is caused by the fact that the hair follicles do not maintain the same direction of growth under the skin. Quite often a hair follicle significantly changes its direction or angle underneath the skin. As seen in FIG. 1, the orientation of the portion of hair shaft 3 above the skin differs from the orientation of the portion of the hair shaft 3 below the skin. Generally, it has been observed that an emergence angle of the FU from the skin is more acute than its subcutaneous course. As a result, aligning the hair harvesting tool 4 with the visible axis of the FU above the skin and advancing the punch based on the visible portion of the hair follicle above the skin, may result in FU transection, damaging it or rendering it unusable. As seen in FIG. 1, advancing the hair harvesting tool 4 along the axis of the hair shaft 3 at an acute angle resulted in transecting (cutting off) a portion of the hair follicle below the skin level containing the hair bulb 2.

It has also been observed that a tool, such as a hollow punch directed at the scalp at high velocity and aligned with a hair follicle positioned at an acute angle: 1) will tend to skive the skin; 2) will create an inconsistent and undesirable asymmetric incision in the skin. For example, the leading edge of the punch will make an incision deeper into the skin than the opposing edge. This is undesirable because the deeper incision with the leading edge may cut into the follicle. This action has been observed with high speed photovideography and clinically.

To avoid or substantially reduce the problems described above, a technique is developed as described herein. The benefits of the described systems and methods includes reduction of the transection rates of follicles during harvesting, preventing harvesting needles from sliding on the body surface (e.g. scalp), scraping the skin surface, or insufficiently penetrating the skin surface due to the acute angles at which needle may approach the surface, as well as improving esthetic results during hair implantation. The "approach angle" of the needle with respect to the body surface, for example, a scalp (as described in more detail in reference to FIG. 4A), is important in both harvest and implant processes. During harvesting, it is desirable to avoid those follicles that are lying almost flat against the scalp, because the needle will tend to skive along the skin during puncture, thereby increasing transection rates. During implantation, it is desirable to match the angles of the existing follicles so that newly implanted hair follicles blend in more naturally.

In both cases it is beneficial to compute a model of the patient scalp (or other relevant body surface) in real-time, and use this model to measure the emergence angle of existing hairs in the field-of-view (FOV) of the camera, as well as the approach angle of the needle with respect to said body surface. In some embodiments, the body surface model is parameterized utilizing a planar model (i.e. represent the patient's scalp as a plane). In other embodiments, the model accounts for the body curvatures and 3D dimensions. Therefore, solutions disclosed herein are in no way limited to the described particular models, provided as examples only.

Figure 2:
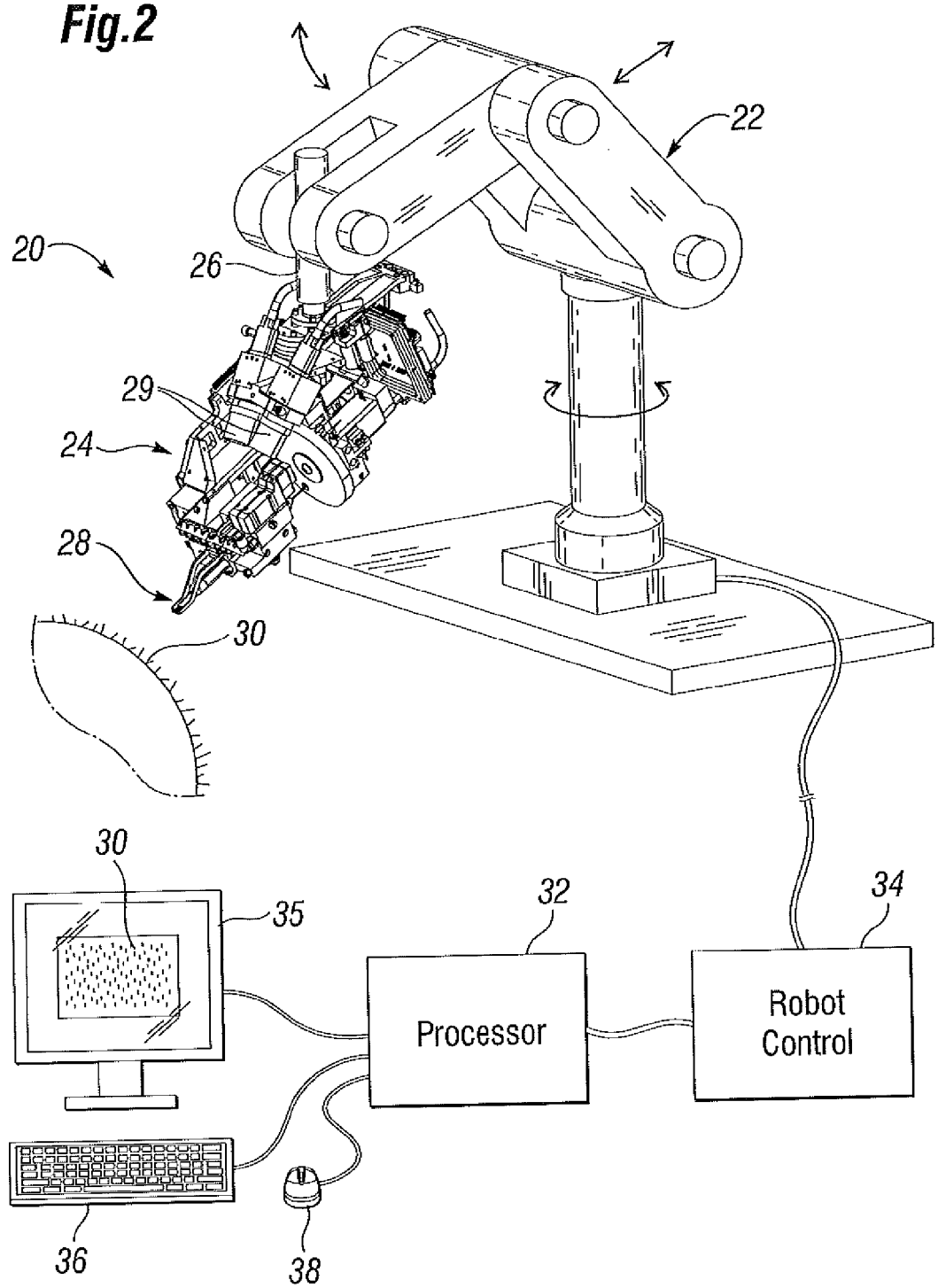
FIG. 2 is a schematic perspective view of one example of the robotic system for use with some embodiments of the invention.

FIG. 2 is a schematic perspective view of one example of the robotic system 20 that could be implemented with the methodology of the inventions described herein. The system 20 includes a robotic arm 22 and an assembly 24 mounted, for example, for rotation on a down tube 26 of the robotic arm. Various arrows are shown to illustrate the movement capabilities of the system 20. Various motors and other movement devices may be incorporated in the assembly 24 to enable fine movements of an operating tip of a tool 28 in multiple directions. The exemplary robotic system 20 further includes at least one imaging acquisition device 29, which is described in more detail below. The image acquisition device may be mounted in a fixed position, or it may be coupled (directly or indirectly) to a robotic arm or other controllable motion device. The operating tip of the tool 28 is shown positioned over a body surface 30, in this case a part of the patient scalp having hair follicles thereon. The tool 28 is any number of the harvesting and/or implanting tools useful for, respectively, removing and/or implanting follicular units from and into the body surface 30. In some embodiments, the harvesting and the implanting tool may be combined in one tool, in other embodiments, these tools may be separate tools.

A processor 32 of FIG. 2, comprises an image processor for processing images obtained from the image acquisition device 29. The processor 32 may also instruct the various movement devices of the robotic arm 22 and the assembly 24, including the harvesting/implanting tool, and act, for example, through a robotic control 34 as schematically shown in FIG. 1 The robotic control 34 may be operatively coupled to the robotic arm and configured to control the motion of the robotic arm, including the motion based on the images or data acquired by the image acquisition device. Alternatively, robotic control 34 may be incorporated as a part of the processor 32, so that all processing and controls of all movements of all the tools, including harvesting tools, the robotic arm and any other moveable parts of the assembly, including those based on the images or data acquired by the image acquisition device, are concentrated in one place. The system 20 may further comprise a monitor 35, keyboard 36, and a mouse 38. The system further comprises an interface adapted to receive an image data, various parts of the system allow an operator to monitor conditions and provide instructions, as needed. A magnified image of the body surface 30 can be seen on the monitor 35. In addition, the system may comprise other tools, devices and components useful in harvesting, and/or implantation of the FU, or in hair treatment planning.

Some non-limiting examples of an image acquisition device 29 shown in FIG. 2 include one or more cameras, such as any commercially available cameras. The image acquisition device may take still images, or it could be a video recording device (such as a camcorder) or any other image acquisition device or sensor. While stereo or multi-view imaging devices are very useful in the systems and methods described herein, it is not necessary to employ such geometries or configurations, and the concepts described herein are not so limited. Likewise, although it is preferred that the image acquisition device be a digital device, it is not necessary. For example, the image acquisition device could be an analog TV camera that acquires an initial image which is then processed into a digital image (for example, via an analog-to-digital device like a commercial-off-the-shelf frame grabber) for further use in the methods of the invention. The image acquisition device may be coupled to a processing system, shown incorporated in the processor 32 in FIG. 2, to control the imaging operation and process image data.

The image processor, which sometimes may be referred to as a processor, may comprise any suitable device programmed and configured to perform the methods described herein. It may incorporate a single or multiple processors to control various subsystems and provide the user interface. For example, the image processor may be programmed with software configured to perform the methods of the invention as further described in more detail. By way of example, and not limitation, a suitable image processor may be a digital processing system which includes one or more processors or other type of device. An image processor may be a controller or any type of personal computer ("PC"). Alternatively, the image processor may comprise an Application Specific Integrated Circuit (ASIC) or Field Programmable Gate Array (FPGA). The image processor may also include memory, storage devices, and other components generally known in the art and, therefore, they do not need to be described in detail here.

Description of the Surface Fit Process and Emergence Angle Determination

Figure 3:
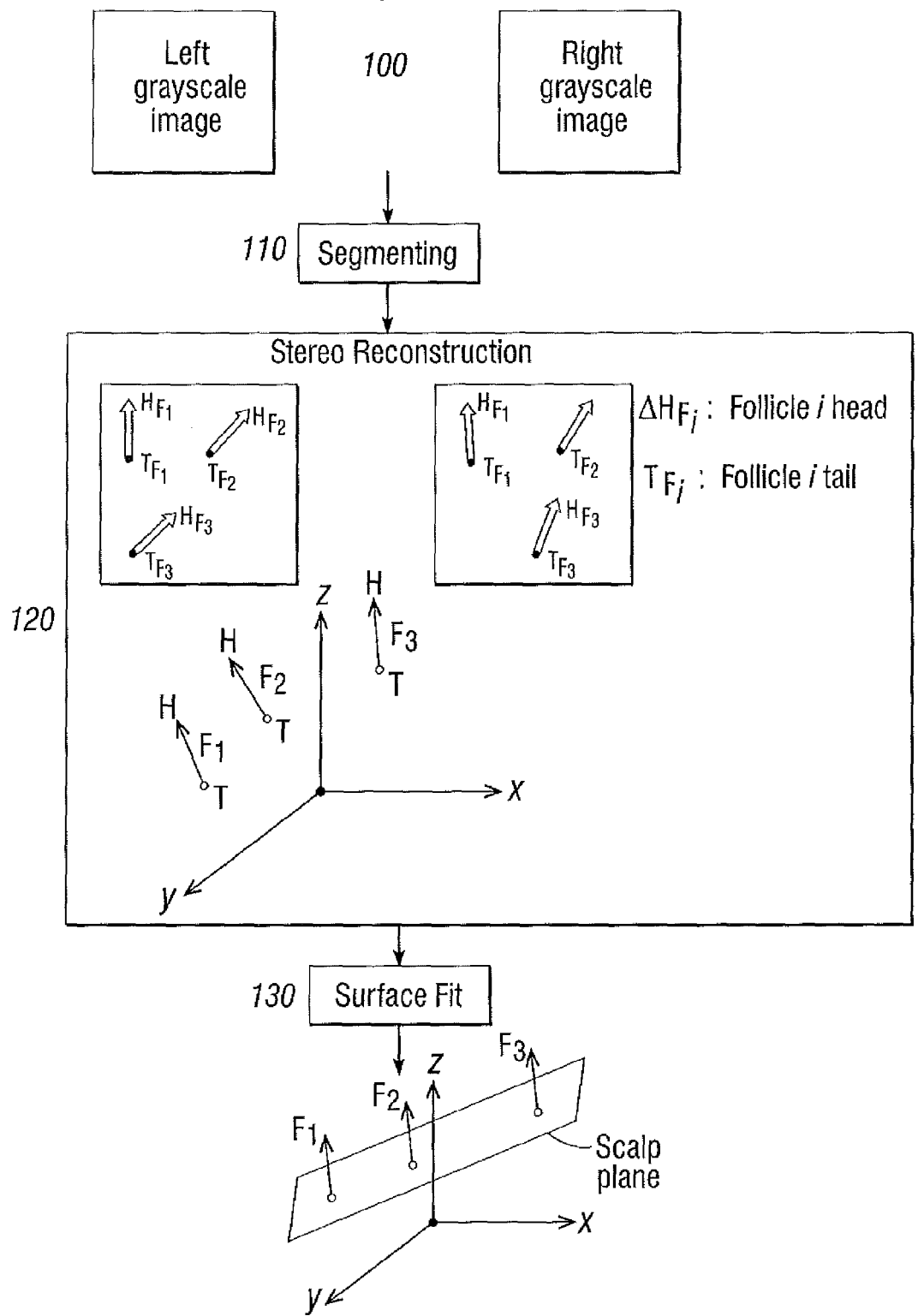
FIG. 3 is a flow chart demonstrating one example of the surface fit process according to the invention.

According to one aspect of the invention, the method for modeling skin or body surface topology from images is provided. The flow chart of FIG. 3 illustrates an example of one embodiment of a surface fitting process used in the inventions described herein. Image acquisition device, for example, as described in reference to FIG. 2 may be used to obtain images of the body surface containing follicular units. In one embodiment, two cameras are used to obtain two stereo grayscale images with each image acquisition event, for example, left and right grayscale images (100). The acquired images are segmented (110). Segmentation may be accomplished, for example, using image segmentation software. Because of physical attributes of a hair follicular unit, its base (i.e., the end emerging from the dermis) can be readily distinguished from its tip as part of the image segmentation process. For example, the base portion has a different profile and is generally thicker than the distal tip portion. Also, a shadow of the follicular unit can typically be identified which, by definition, is "attached" at the base. At (120) stereo reconstruction is performed to locate the position of one or more follicular units of interest present in the field of view (FOY). For example, one process of stereo reconstruction that could be used in the present invention is described in the commonly owned co-pending patent application published as US 2007/0106306A1 on May 10, 2007, which is incorporated herein by reference. According to the above-mentioned process, the locations of the centers of the hair follicles are identified and matched in both the left and right rectified images. Each follicle has a "tail"—the point at which the hair exits the body surface, e.g. scalp, and a "head"—the tip of the hair shaft. The head and tail of each hair follicle is identified in both the left and right images, wherein the three dimensional coordinates of the head and tail of the hair follicle may be calculated. By utilizing known camera geometry, 3D coordinates of each relevant FU is determined, including 3D coordinates of each tail and head are determined. Stereo reconstruction is just one example of locating the position of follicular units of interest. For example, it is possible to obtain 3D information about the follicles in the field-of-view by utilizing more than two images. Alternatively, 3D data may also be obtained from one or more grayscale pictures by augmenting the vision system with a laser "range-finder" device.

Once a list of relevant hair follicles and the 3D coordinates of their heads and tails is known, a surface fit to the tail coordinates of the FU may be performed (130). In the example of FIG. 3, it is assumed that the portion of the scalp being imaged is flat and the surface fit is performed using, for example, a least-squares technique. In the example shown the surface represents the patient scalp. The set of tail positions may be fit to a function of the following form:

(1) $Ax+By+Cz+D=0$      [Equation 1]

Equation 1 defines a plane and hence the system represents the patient's scalp as a planar surface. In general the fitting function could be that of a higher-order polynomial (e.g. a $2^{nd}$ order quadric, or higher) that takes into account the natural curvature of the scalp. Alternatively, one could fit a mesh to the set of tail positions, which would be useful for a generally curved surface with a fair amount of "local bumps" and "grooves," for example, due to the application of topical anesthetic or tumescence in case of hair transplantation procedures. While the example above employs the least-squares technique to perform the surface fit, any number of mathematical analyses well known to those skilled in the art may also be used.

Figure 4A:
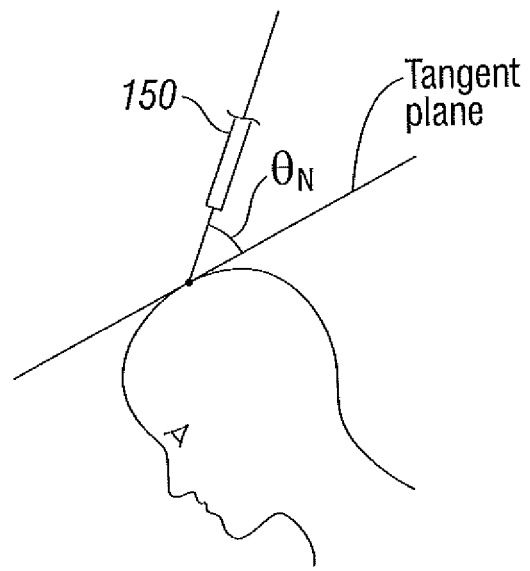
FIGS. 4A and 4B are schematic views showing an emergence angle of the follicular unit(s) of interest and a tool approach angle.
Figure 4B:
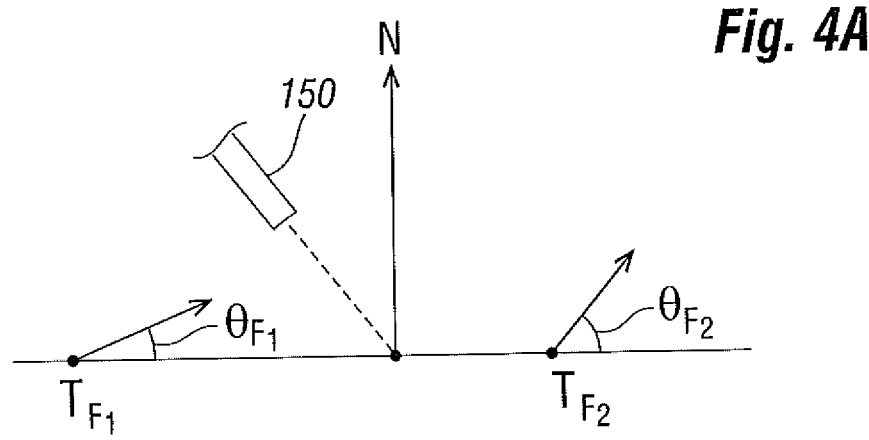

The surface model (planar surface, quadric, higher-order polynomial, mesh, parametric, etc.) may be used to compute an "emergence angle" for each follicle unit of interest and a "tool approach angle" of the tool used in the procedure (e.g. hair harvesting tool, hair implantation tool). FIGS. 4A and 4B illustrate the above angles for a planar fit example. Higher-order polynomial fits, such as a quadric, would use the tangent plane at the point-of-contact with the scalp surface to compute the emergence angle measurement. In FIG. 4A, $\theta_N$ represents an approach angle of the tool 150 (such as a needle) from the body surface, such as scalp. In FIG. 4B, $\theta_{F1}$ represents an emergence angle of the hair follicle 1 from the scalp, while $\theta_{F2}$ represents an emergence angle of the hair follicle 2 from the scalp, and an N arrow represents a vector normal to the scalp surface.

The description above is based on how to surface fit "small" regions of the skin, for example, patient's scalp, where "small" is a region of the scalp on the order of approximately 1 cm². For significantly larger regions, for example, an area of 3.5 cm², a planar assumption may not work because in reality the body surface, especially the surface of the head, is not flat but curved. In this case, the curvature may be approximated by fitting the hair tail coordinates to a 2D semispherical surface, described mathematically as a 2D quadric. The measured follicle tail coordinates may be taken and a quadric fitting to a 2D parabola of the form may be performed, for example, as follows:

$$z = A + R(x-x_0)^2 + R(y-y_0)^2,$$

where the apex of the parabolic surface is $(x_0, y_0)$, its value at the apex is A, and the radius-of-curvature of the patient's scalp in the imaged region is R.

Usage of Surface Fit Process in Harvesting of Follicular Units

Figure 5A:
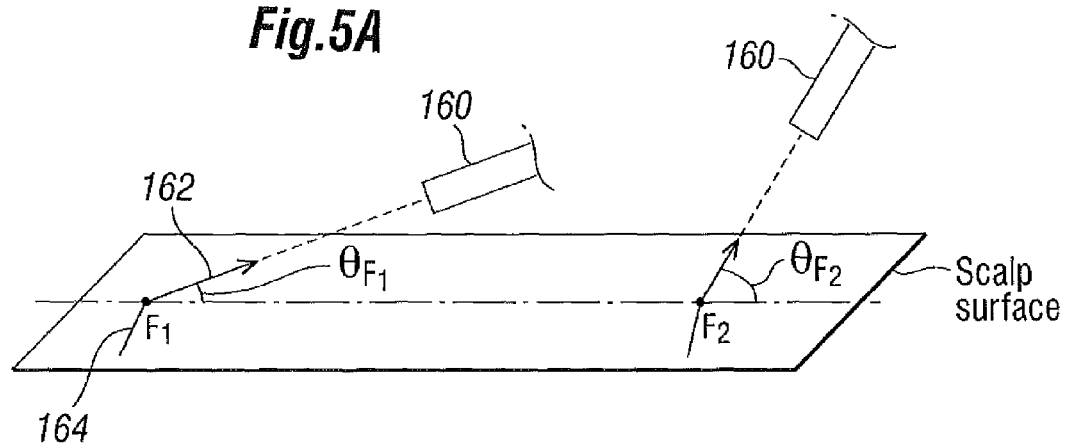
FIGS. 5A and 5B demonstrate examples of the tool orientation relative to the FUs according to the invention.

It was determined that there exists a cut-off point (or a range of cut-off points for various body surfaces) at which the risk of transection becomes high if one tries to fully align a tool, such as a needle, with a given hair whose emergence angle θ is too small. FIG. 5A depicts this situation. Follicular unit $F_1$ has "above the skin" shaft portion 162, "below the skin" shaft portion 164 and an emergence angle $\theta_{F1}$. As could be seen from FIG. 5A, the emergence angle $\theta_{F1}$ is fairly acute, and there is a substantial difference between the directions of the shaft portions 162 and 164, the below the skin shaft portion 164 having less acute subcutaneous direction. The follicular unit $F_2$, on the other hand, has more upright emergence angle and its "above the skin" and subcutaneous portions of the shaft are closer to parallel. The risk of transection for follicle $F_1$ is comparatively higher than that of $F_2$ because $F_1$ is shown lying almost flat on the scalp. When fully aligned to $F_1$, the tool 160, such as a harvesting needle, will have a greater propensity to skive or shave along the surface during the puncture. Moreover since the shaft and the bulb underneath this follicle is more closely oriented to the surface normal then what might be suspected given the shaft's orientation out of the skin, the chance of the tool 160 transecting $F_1$ is comparatively greater. In contrast, if the needle 160 completely aligns to $F_2$, a risk of transecting this follicle is reduced because it is more likely that the tool 160 will be following the subcutaneous direction of the follicle $F_2$.

While performing hair harvesting, especially when using an automated system, such as a robotic system, it is often desirable to stretch the skin around the area of location of the follicular unit to be harvested. This could be done using a skin tensioner device. It has been observed that when the skin tensioner device is used, it tends to even further reduce the emergence angle of the follicles in the area where the skin tensioner device is applied. For example, in some cases, skin tensioner device application reduces the emergence angle of the relevant FUs in the range of 5-12 degrees, in some cases in the range of 7-10 degrees. That is, if the "natural" emergence angle of the hair at issue is 50 degrees, then after application of the skin tensioner device, the emergence angle measures at approximately 43 degrees. As a result it even further increases the number of hair follicles which will be potentially transected if the user aligns the tool with such hair follicles. Similarly, injection of saline into the donor/recipient area may cause changes in the "natural" emergence angle of hairs. Skin tensioning devices and saline injections may be used not only in the robotic hair transplantation procedures but also with partially automated procedures and procedures using hand-held devices, therefore, this issue of a large number of follicular units having an emergence angle of 45° or less, is applicable to all types of the hair transplantation procedures.

Figure 5B:
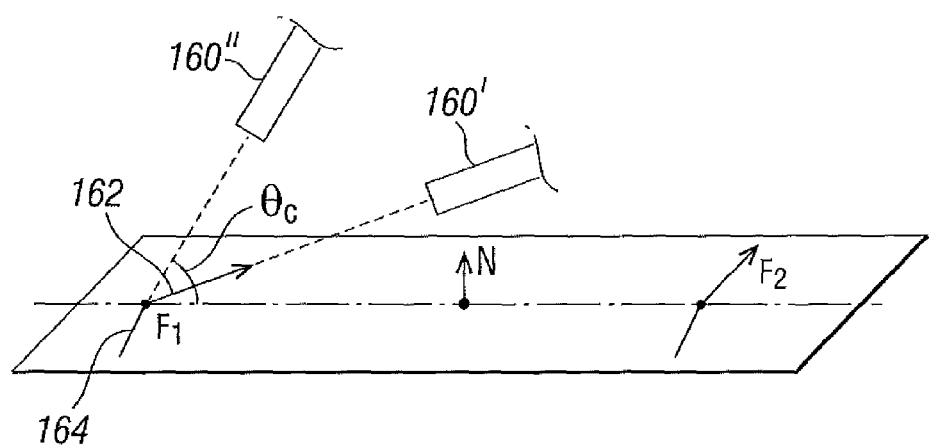

FIG. 5B illustrates a method of orienting the tool relative to the FU of interest according to the invention. Based on various factors and certain characteristics, including the geometry and design of the tool or mechanism used in the procedure, the force required to facilitate the desired skin surface penetration, measurements of the emergence angles of the existing hair in the relevant area, it was determined that there exists a cut-off tool approach angle $\theta_c$ (also referred to as minimum approach angle of a tool) below which the tool shall not be aligned with the relevant FU. It is so because, for example, the risk of transection, not cutting the tissue, or creating asymmetric dissections becomes too high. In other words, if the emergence angle of the follicle is less than $\theta_c$, instead of aligning the axis of the tool with the visible portion of the shaft of the follicular unit, the user shall orient the tool with such cut-off tool approach angle $\theta_c$. It is suggested that the cut-off or minimum tool approach angle $\theta_c$ must be selected in the range of, approximately, 40° to 65° and preferably, in the range of 45° to 55°, and even more preferably, in the range of 50° to 55° for certain tools and applications. As a practical matter, a vast majority of the harvested hair, especially when employing the skin tensioner, will have an emergence angle smaller than the suggested $\theta_c$. In these situations, a tool may be oriented relative to the FU of interest by restricting the orientation angle of the needle to be not less than the cut-off approach angle $\theta_c$. In certain applications, it may be desirable, for the reasons mentioned above, to add approximately 15-20° to the emergence angle of the relevant existing hair follicle to determine a desirable minimum approach angle $\theta_c$. For example, if the hair emergence angle is 35°, a minimum approach angle of about 50° may be used to produce acceptable harvesting results.

In FIGS. 5A and 5B, in the case of $F_1$, because $\theta_{F1} < \theta_c$, the system does not align to the $F_1$ hair vector and instead orients the axis of the needle or punch 160" assuming that the $F_1$'s emergence angle is $\theta_c$. The calculation for positioning the needle precisely within the plane formed by $F_1$ perpendicular to the scalp surface uses the normal to the surface N.

According to one aspect of the invention as described above, a method of orienting a tool for harvesting is provided. Such method could be used in procedures using systems, such an a robotic system shown as an example in FIG. 2, as well as various other automated, partially automated or manual systems, including using a hand-held devices, as described below in reference to FIG. 8. As a preliminary step, an image of the follicular unit(s) of interest is obtained. That may be accomplished by any technique known in the art. For example, in some embodiments a robotic arm (or a portable device in the physician's hand) with the attached image acquisition device may be positioned so that the harvesting or implantation region is in focus for the cameras. According to one embodiment of the method, an emergence angle of a FU of interest is determined, a minimal approach angle of a tool for harvesting follicular units is chosen and the emergence angle of the FU of interest is compared with the minimum approach angle of the tool. Based on a result of the comparison of the emergence angle of the FU of interest with the minimum approach angle of the tool, the tool is oriented relative to the FU of interest. If the emergence angle of the FU of interest is less than the selected minimum approach angle, the tool is oriented to the minimum approach angle, and it is not aligned with the actual emergence angle of the FU. In some embodiments, the tool may be oriented by automatically moving a robotic arm to which the tool is coupled. In other embodiments an adjustment mechanism is actuated to orient a hand-held tool according to the above method. Various examples of the adjustment mechanism are described in reference to FIG. 8.

According to another aspect of the invention, a method for harvesting follicular units from a body surface is provided. Such method comprises positioning a harvesting tool having a lumen over a FU of interest. Such FU of interest has an elongated axis. The method further comprises orienting the harvesting tool relative to the elongated axis of the FU based on a result of a comparison of an emergence angle of the FU with a selected minimum approach angle of the harvesting tool. The harvesting tool is inserted into the body surface about the FU of interest to be harvested and the FU is removed from the body surface. Determining an emergence angle of the FU may be accomplished by using image-generated topological skin models, as described above. Orienting the harvesting tool may be accomplished automatically using, for example, a robotic system, or it could be done manually if a hand-held tool is used as described below in reference to FIG. 8.

Usage of Surface Fit Process in Implantation of Follicular Units

During implantation, to improve quality and appearance of the implanted hair grafts, it is desirable to figure out the location and desired orientation (or emergence angle) of the hair follicles to be implanted based on the density, location and emergence angles of the pre-existing hair in the area of the implant sites (recipient area), for those cases where pre-existing hair exists near the implant sites. However, as with the hair harvesting, if the emergence angle of the pre-existing hair is very low, such as below, for example 40-45°, matching the approach angle of the implantation tool to the emergence angles of the pre-existing hair may be undesirable and will not provide satisfactory results. For example, approaching the body surface, such as scalp with the implantation tool at very low angles may result in the tool sliding, scraping the scalp, or not penetrating to the desired depth, and therefore preventing correct implantation. To eliminate these situations, the following method has been developed. According to some embodiments of the invention, bald spots on the fitted surface are identified and then the proposed fake or "virtual hairs" (sites) having emergence angles that match the emergence angles of the existing hair are generated. These virtual hairs need to be generated so they lie on the scalp surface, so that the implantation tool may be then aligned to the sites just prior to the actual implantation. FIG. 6 is a depiction of this procedure and it is based on an assumption that the patient has some pre-existing hair in the area of the proposed implant site. Similarly to the processes described in reference to FIG. 3, images containing existing "real" follicular units are obtained, processed, segmented and hairs in the FOV (denoted as $F_i$ in FIG. 6) are identified. At 200, the image processor analyzes images, for example, stereo images, and identifies a set of bald spots where candidate implant sites can be generated. ($S_i$ in FIG. 6). The existing hairs are subsequently reconstructed into their 3D coordinates (at 210) and a surface fit is performed (at 220), for example, as explained in reference to FIG. 3. At 230 implant sites are created by generating virtual hairs. In some embodiments, in generating virtual hairs, one may choose upfront not to match automatically their orientation to the orientation of the pre-existing hair, but rather compare each relevant emergence angle to the recommended minimum approach angle of the tool, and generates virtual hairs such that they never appear below the minimum approach angle of the tool. The recommended minimum tool approach angle may be selected in the same ranges as previously provided, for example, between 45° and 65° depending upon a specific area of the scalp that is being implanted. In other embodiments, virtual hairs are initially generated at least partially based on the emergence angles of the pre-existing hair. However, during the step of orienting the implantation tool, the emergence angle of the virtual hair is compared to the suggested minimum approach angle of the tool, and the tool is oriented for implantation based on the results of such comparison, as described above. If a robotic system for hair transplantation is used, then the robotic arm with the implantation tool orients itself appropriately (depending on the comparison between an emergence angle of these virtual hairs and the minimum tool approach angle). Alternatively, in case of the procedure conducted using a hand-held device, the user holding the implantation tool orients the tool for implantation based on the results of the same comparison. The operator may also choose to move these automatically generated implant sites if so desired. In order to make this movement physically meaningful, as the operator uses the mouse (or some other pointing device) to move the individual hair(s) their tail positions are altered such that they lie on the fitted surface that represents the patient's scalp.

The aforementioned process is viable if there exists a multitude of pre-existing real hairs in the FOV. Strictly speaking, there must be at least three real hairs for a planar fit but practically speaking one requires at least 3×, or more for a robust regression analysis. If the patient is completely bald or highly sparse, the system may use external markers (fiducials) or anatomical landmarks (e.g. moles, scars, etc.) to perform the surface fit. FIG. 7 is an illustration of this methodology using fiducials placed, for example, on the patient's scalp (see 300). In some embodiments, fiducials may be placed, for example, on a skin tensioner used during the procedure instead of the actual body surface, such as scalp. At 310 images of the body surface with fiducials is acquired, at 320 previously described processing, including segmentation, determination of fiducials and bald spot locations is performed. At 330, 3D reconstruction is done and at 340 a surface fit is performed. After the surface fit is performed, virtual hairs (or sites) are generated as shown at 350 and as described above in reference to FIG. 6. As before, either the emergence angle of such virtual hair, or the orientation of the implantation tool is determined based on taking into the account the minimum approach angle of the implanting tool, such as needle. One of the input considerations is the area of the scalp that is being implanted. More acute angles/orientations are desirable in the hairline and the temple region. Less acute angles are common in the top of the scalp. The steps of hair implantation (whether using automated or manual systems) may be the same or similar to those described in reference to FIG. 6. In one embodiment used as an example, the method for orienting a tool for implanting follicular units relative to a body surface may comprise using fiducial markers to generate one or more virtual FU having an emergence angle; selecting or using a pre-selected minimum approach angle of a implanting tool for implanting follicular units; identifying the emergence angle of the one or more virtual FU to be not less than the minimum approach angle of the implanting tool; and orienting the implanting tool with the identified emergence angle of the one or more virtual FU.

In certain embodiments, a combined procedure may be implemented using previously described methods in reference to hair harvesting and further comprising the surface fit process and/or emergence angle determination in orienting a tool for implanting FUs, in generation of the virtual hairs, and in the creation of the implant sites.

The image processor, such as any of those described in reference to FIG. 2, processes the obtained image to identify the desired information about the follicular unit of interest. The image processor may be configured for determining an emergence angle of the follicular unit, choosing a minimal approach angle of a tool for harvesting follicular units, and comparing the emergence angle of the follicular unit to the minimal approach angle of the tool. Based on the results of such comparison, it may be configured to instruct the robotic arm with the attached harvesting tool (or a hand-held tool in manual procedures) on how to orient relative to the follicular unit. The image processor may be also configured to practice methods of the invention during hair implantation, as described above. For example, it may be configured for determining an emergence angle of the pre-existing follicular unit, choosing a minimal approach angle of a tool for implanting follicular units, and comparing the emergence angle of the follicular unit to the minimal approach angle of the tool. Based on the results of such comparison, it may be configured to instruct the robotic arm with the attached implantation tool (or a hand-held tool in manual procedures) on how to orient accordingly.

The inventions disclosed herein are also directed to an image processor comprising one or more modules or components for executing operations on the image data. The above one or more modules may include instructions for one or more of the following: receiving an image containing a FU; determining an emergence angle of the FU; selecting a minimal approach angle of a tool used in hair transplantation procedure; comparing the emergence angle of the FU with the minimum approach angle of the tool; and orienting the tool relative to the FU based on a result of the comparison of the emergence angle of the FU of interest with the minimum approach angle of the tool. The above-mentioned components or modules may comprise an emergence angle determination component, angle comparison component (compares an emergence angle of the FU of interest with a selected minimum approach angle of the tool), tool orientation component. Various described modules and components may be a part of single software or hardware product.

The image processor as described above could be used in conjunction with various manual, partially automated and fully automated (including robotic) hair transplantation and treatment systems and devices, including but not limited to systems for hair harvesting, or hair transplantation. Similarly, the image processor of the present invention could be used with hair treatment planning systems.

While the inventions described herein are especially useful in robotically operated systems for harvesting/transplanting hair, it will also provide great benefit to a physician who harvests follicular units using a manual FUE technique with manual/partially/fully automated hand-held tools, as it will guide the physician in adjusting an angle of insertion of the tool to avoid transecting or otherwise damaging the follicular unit or tissue to be harvested. Similarly, it will benefit a physician who performs implantation using a hand-held device.

Figure 8:
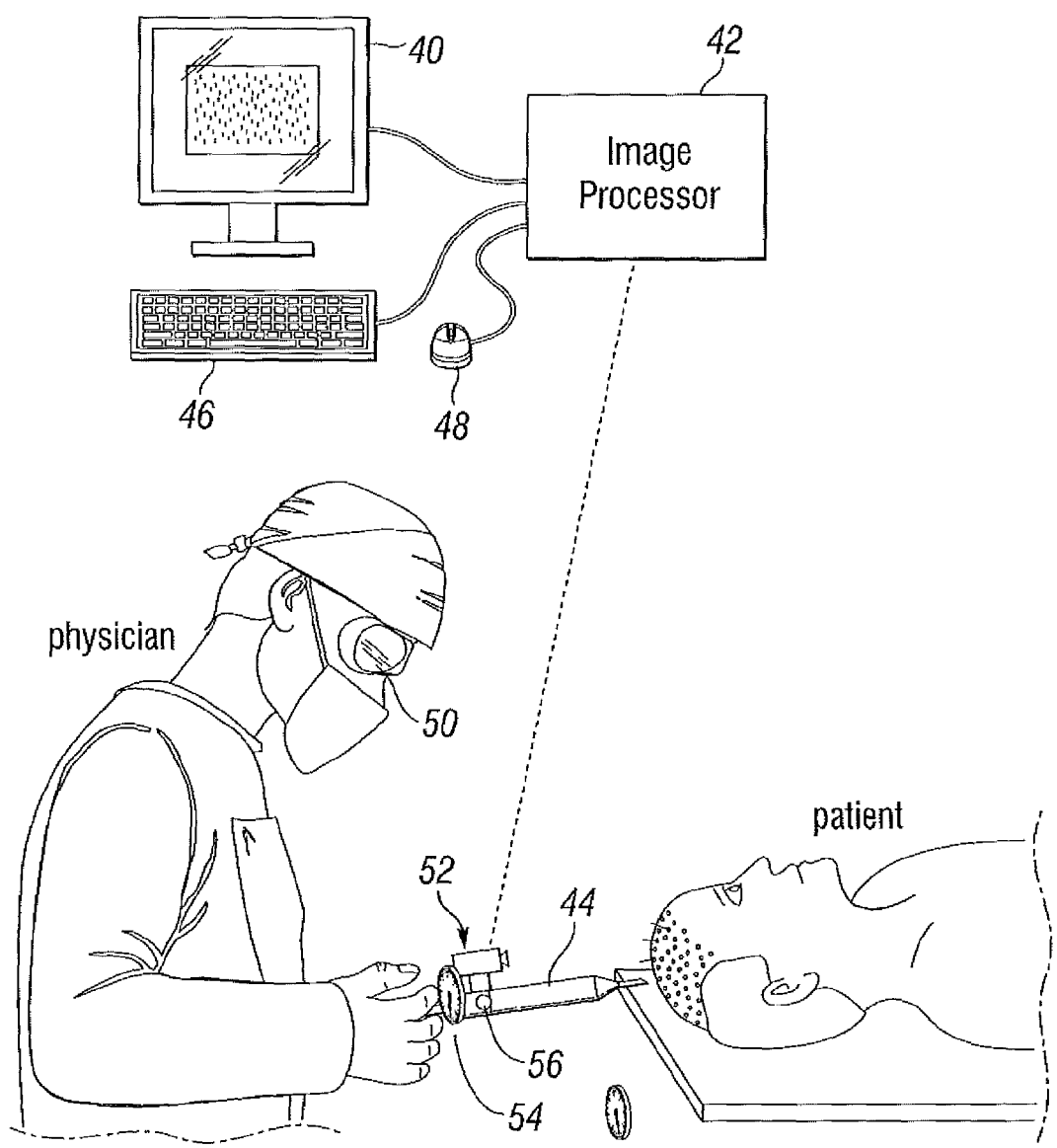
FIG. 8 is a schematic view of an exemplary embodiment of a hair harvesting/implantation system for use with hand-held devices for hair transplantation.

One such implementation is shown as an example in FIG. 8. In this embodiment, a physician is conducting a manual operation on the patient using a hand-held tool 44, for example, a harvesting tool and/or an implanting tool, and he/she may wear the typical glasses 50 that have high-magnification. An image acquisition device 52, such as one or more cameras, may be attached to the hand-held instrument or tool 44. In some additional embodiments, it may be a stand-alone image acquisition device. The image processor, such as the computer 42, may execute various steps as described herein and perform the image analysis and processing, including 3D reconstruction, surface fit, determining an emergence angle of the existing follicular units, comparing the emergence angle with the minimum approach angle of the tool and determining the angle offset between the above two measurements, or determining the desired emergence angle for the virtual hairs in case of the hair implantation procedure. The monitor 40 may display the highlighted follicular unit(s), fiducials locations, or bald spots, as well as all other useful data, for example, emergence angle of the follicular unit(s) to be harvested, as well as the proposed orientation of the hand-held tool relative to such follicular unit(s) to be harvested or an adjustment angle/distance required to move the tool into the proper harvesting position relative to the FU.

Similarly, in case of the implanting procedure, the monitor 40 may display additional parameters, including those previously discussed, useful in conducting hair implantation for achieving correct tool orientation and implantation angles. Guided by the information displayed on the monitor, a physician may adjust the tool approach angle and orientation of the harvesting tool in his/her hands relative to the FU selected for harvesting, or orientation of the implanting tool in his/her hands for implanting. Orienting the hand-held tool may be actuated by a variety of different mechanisms, for example, mechanical or electronic mechanisms. In some embodiments, a body of the hand-held tool may be operatively connected to or supported by a guide structure having an angular indicator. Guided by the previously determined angle of insertion displayed on the monitor, the user may rotate the angular position of the tool until the reading on the angular indicator matches the angle on the monitor. The tool may be permanently or removably connected to the guide structure and angular indicator. Some embodiments may use a circular dial having angular indicia markings, in other embodiments it may be an electronic display with arrows and lights. FIG. 8 schematically represents as an example an indicator 54 mounted on the hand-held tool 44. In some alternative embodiments, the hand-held tool may comprise a transducer or other sensor (shown as 56 in FIG. 8) that electronically connects to the imaging system. Alternatively, the sensor 56 may be a part of the imaging system 52.

As will be appreciated by those skilled in the art, the methods of the present invention may be embodied, at least in part, in software and carried out in a computer system or other data processing system. Therefore, in some exemplary embodiments hardware may be used in combination with software instructions to implement the present invention. For example, an article of manufacture of the present invention may comprise a machine-accessible medium including data that, when accessed by a machine, cause the machine to perform operations, such as determining an emergence angle of a FU of interest; choosing a minimal approach angle of a tool (e.g. a tool for harvesting follicular units, or a tool for implanting follicular units, or a combination of both); comparing the emergence angle of the FU of interest with the minimum approach angle of the tool; and orienting the tool relative to the FU of interest based on a result of the comparison of the emergence angle of the FU of interest with the minimum approach angle of the tool.

A machine-readable medium may be used to store software and data which causes the system to perform methods of the present invention. The above-mentioned machine-readable medium may include any suitable medium capable of storing and transmitting information in a form accessible by processing device, for example, a computer. Some examples of the machine-readable medium include, but not limited to, magnetic disc storage, flash memory device, optical storage, random access memory, etc.

The foregoing illustrated and described embodiments of the invention are susceptible to various modifications and alternative forms, and it should be understood that the invention generally, as well as the specific embodiments described herein, are not limited to the particular forms or embodiments disclosed, but to the contrary cover all modifications, equivalents and alternatives falling within the scope of the appended claims. By way of non-limiting example, it will be appreciated by those skilled in the art that particular features or characteristics described in reference to one figure or embodiment may be combined as suitable with features or characteristics described in another figure or embodiment. Similarly, the invention is not limited to the use of a robotic system including a robotic arm, and that other automated, semi-automated or manual systems may be utilized.

While the invention has been described in its preferred embodiments, it is to be understood that the words which have been used are words of description and not of limitation. Therefore, changes may be made within the appended claims without departing from the true scope of the invention.

What is claimed is:

1. A system for hair transplantation, comprising:
    an interface adapted to receive an image data containing a follicular unit (FU); and
    an image processor comprising one or more modules for executing operations on the image data, the one or more modules including instructions for:
        determining an emergence angle of the FU;
        selecting or using pre-selected minimal approach angle of a tool used in transplantation of follicular units;
        comparing the emergence angle of the FU with the minimum approach angle of the tool; and
        determining the orientation of the tool based on a result of the comparison of the emergence angle of the FU with the minimum approach angle of the tool.

2. The system of claim 1, further comprising an image acquisition device.

3. The system of claim 1, wherein the system is a robotic system and it further comprises a robotic arm, and wherein the tool is operatively connected to the robotic arm.

4. The system of claim 1, further comprising a monitor configured to display the results of the comparison of the emergence angle of the FU with the minimum approach angle of the tool.

5. The system of claim 1, wherein the system comprises the tool, and wherein the tool is a hair harvesting tool, a hair implantation tool, or a combination of both hair harvesting and hair implantation tool.

6. The system of claim 1, wherein the FU comprises a head and a tail, and the instructions for determining the emergence angle of the FU further comprise determining 3D coordinates of the head and tail of the FU and performing a surface fit to the tail coordinates.

7. The system of claim 1, wherein the FU is a virtual hair graft, the system further comprises instructions for generating the virtual hair.

8. The system of claim 7, wherein the virtual hair graft is generated such that its orientation is at or above the minimum approach angle of the tool.

9. The system of claim 5, further comprising an angle indicator and wherein the tool is operatively connected to the angle indicator.

10. The system of claim 5, further comprising mechanical or electronic mechanisms to orient the tool.

11. The system of claim 1, wherein selecting or using the pre-selected minimal approach angle of the tool comprises adding a number of degrees to the emergence angle of the FU.

12. The system of claim 1, wherein the minimum approach angle of the tool is between 40 degrees and 65 degrees.

13. The system of claim 1, wherein the one or more modules comprise instructions for creating a model of a body surface comprising the FU and using the model to determine the emergence angle of the FU on the body surface.

14. A system for hair transplantation comprising:
   an image acquisition device for acquiring image data containing a follicular unit (FU); and
   an image processor comprising one or more modules for executing operations on the image data, the one or more modules comprising instructions for:
      determining an emergence angle of the FU;
      selecting or using a pre-selected minimal approach angle of a tool used in transplantation of follicular units;
      comparing the emergence angle of the FU with the minimum approach angle of the tool; and
      determining the tool orientation based on a result of the comparison of the emergence angle of the FU with the minimum approach angle of the tool.

15. The system of claim 14, further comprising a monitor for displaying the FU, the determined emergence angle of the FU, the determined tool orientation, or the results of comparison of the emergence angle of the FU with the minimum approach angle of the tool.

16. The system of claim 15, further comprising the tool, wherein the tool is a hand-held device and the monitor is attached to the tool.

17. The system of claim 14, further comprising the tool, wherein the tool is a hand-held harvesting device operatively connected to or supported by a guide structure having an angular indicator.

18. The system of claim 14, further comprising a transducer or other sensor that electronically connects to the image acquisition device or forms a part of the image acquisition device.

19. The system of claim 14, wherein the system is a robotic system and it further comprises a robotic arm and the tool, and wherein the tool is operatively connected to the robotic arm.

20. The system of claim 14, wherein the FU is a virtual hair graft, the system further comprises instructions for generating the virtual hair.

21. The system of claim 14, wherein selecting or using the pre-selected minimal approach angle of the tool comprises adding a number of degrees to the emergence angle of the FU.

22. An article of manufacture comprising a machine-accessible medium including data that, when accessed by a machine, cause the machine to perform operations, comprising:
   determining an emergence angle of a FU of interest;
   selecting or using a pre-selected minimal approach angle of a tool for harvesting or implanting follicular units;
   comparing the emergence angle of the FU of interest with the minimum approach angle of the tool; and
   determining a proposed orientation of the tool based on a result of the comparison of the emergence angle of the FU of interest with the minimum approach angle of the tool.

* * * * *